US00PP24052P3

(12) United States Plant Patent
Banuelos et al.

(10) Patent No.: US PP24,052 P3
(45) Date of Patent: Dec. 3, 2013

(54) *OPUNTIA* PLANT NAMED 'SELENO-RED'

(50) Latin Name: *Opuntia ficus-indica*
Varietal Denomination: Seleno-Red

(75) Inventors: Gary Banuelos, Fresno, CA (US); John Leonard Freeman, Fresno, CA (US); John Diener, Five Points, CA (US)

(73) Assignees: California State University, Fresno, Fresno, CA (US); Red Rock Ranch, LLC, Five Points, CA (US); USDA, Washington, DC (US)

( * ) Notice: Subject to any disclaimer, the term of this patent is extended or adjusted under 35 U.S.C. 154(b) by 80 days.

(21) Appl. No.: 13/506,030

(22) Filed: Mar. 21, 2012

(65) Prior Publication Data

US 2013/0254959 P1 Sep. 26, 2013

(51) Int. Cl.
*A01H 5/00* (2006.01)

(52) U.S. Cl.
USPC ..... Plt./156

(58) Field of Classification Search
USPC ..... Plt./156
See application file for complete search history.

(56) References Cited

U.S. PATENT DOCUMENTS

PP21,760 P2 3/2011 Felker
PP21,834 P2 4/2011 Felker
PP21,964 P3 6/2011 Felker
PP22,077 P3 8/2011 Felker

OTHER PUBLICATIONS

Banuelos, Ajwa, Zambruski, Selenium accumulation by brassica napus grown in Se-laden soil from different depths of Kesterson Reservoir. Journal of Contaminated Soil. 71:481-496. 1998. USA.
Shannon, Banuelos, Draper, Ajwa, Jordahl, Licht. Tolerance of highbred poplar (populous) trees irrigated with varied levels of salt, selenium and boron. International Journal of Phytoremediation. 1:273-288. 1999. USA.
Banuelos. Irrigation of broccoli and canola with boron and selenium-laden effluent. Journal of Environ Qual. 31: 1802-08. 2002. USA.
Steiner, Banuelos. Registration of ARS-NLT-Salt and ARS-NLT-Salt/B Saline tolerant Narrow-Leaf Trefoil Germplasm. Journal of Crop Sci. 43:1888-89. 2003. USA.
Banuelos and Lin. Culvation of Indian Fig *Opuntia* in Selenium-laden agricultural drainage sediments under field conditions. Journal of Soil and Land Management. 26:167-75. 2010. USA.
Felker, et al. Comparison of *Opuntia ficus indica* varieties of Mexican and Argentine origin for fruit yield and quality in Argentina. Journal of Arid Environments. 60:505-22. 2005. USA.
Parish and Felker. Fruit quality and production of cactus pear (*Opuntia* spp) clones selected for increased frost hardiness. Journal of Arid Environments. 37:123-143. 1997. USA.
Feugang, et al. Nutritional and medicinal use of cactus pear *Opuntia* spp. cladodes and fruit. Frontiers in Bioscience. 11:2574-89. 2006. USA.
Zou, et al. Cactus pear—a natural product in cancer chemoprevention. Nutrition Journal. 4:25, doi:10.1186/1475-289-4-25. 2005. USA.
Stadtman. Selenium-dependent enzymes. Annual Review Biochemistry. 49:93-110. 1980. USA.
Ip and Ganther. Relationship between the chemical form of selenium and anticarcinogenic activity. Cancer Chemoprevention. Eds: Wattenberg, et al. CRC Press. Boca Raton, Florida, USA. 1992.
Clark, et al. effects of selenium supplementation for cancer prevention in patients with carcinoma of the skin. Journal of American Medical Association. 276: 1957-63. 1996. USA.

*Primary Examiner* — Annette Para
(74) *Attorney, Agent, or Firm* — Grace Liu

(57) ABSTRACT

A new and distinctly salt and boron tolerant cultivar of prickly pear (*Opuntia ficus-indica*), named 'Seleno-Red,' is particularly distinguishable by its ability to tolerate and grow in high concentration of salt, boron and selenium-laden soil. The cultigen was originally discovered by stringent selection of randomly harvested cladodes (modified stems) and potentially from isolation of a single unique cladode or sport that exhibited high levels of salt and boron tolerance necessary for survival, and then propagated into the 'Seleno-Red' cultivar. The cladodes were originally randomly harvested from different individual plants and screened from within a naturally segregating wild population or accession. The 'Seleno-Red' cultivar has orange-red flowers, mature green cladodes without glochids, and red-purple fruit. When grown in a saline/selenium-laden soil, the spineless 'Seleno-Red' cultivar absorbs high concentrations of natural-occurring selenium, volatilizes selenium, and produces edible cladodes and fruit enriched with potential anti-carcinogenic forms of organic selenium.

3 Drawing Sheets

Latin name of the genus and species of the plant claimed: *Opuntia ficus-indica.*

Cultivar denomination: 'Seleno-Red'.

STATEMENT REGARDING FEDERALLY SPONSORED RESEARCH OR DEVELOPMENT

Selection and Development of the 'Seleno-Red' cultivar was sponsored by federal research at the USDA-ARS and supported by State of California funds in the form of grants from the California State University Fresno Agricultural Research Initiative and the California Department of Water Resources.

BACKGROUND OF THE INVENTION

1. Field of the Invention

In the last decade a large variety of individual plants from numerous accessions of naturally occurring populations have been evaluated for salt and boron tolerance and accumulation of selenium. These include; mustard and canola (Banuelos et al., 1998), poplar trees (Shannon et al., 1999), broccoli (Banuelos et al., 2003), birdsfoot trefoil (Steiner and Banuelos, 2003), and Indian Fig *Opuntia* (Banuelos and Lin, 2010) that were tested under typical poor quality soil conditions present in agricultural drainage sediment and in the Westside of the central valley. The identification of new crops is a prerequisite for the agricultural use of over 500,000 acres of fallowed and drought-stricken hypersalinized soils in the relevant region of California. Importantly, plants that are salt and boron tolerant and require minimum water, are top priority for growers in this part of California.

2. Description of the Relevant Art

*Opuntia ficus-indica* cultivar selections have been previously identified and described (Felker et al., 2005; Parish and Felker, 1997). Four U.S. Plant Patents were issued for newly developed cactus pear varieties (U.S. Plant Pat. No. 21,760 P2, U.S. Plant Pat. No. 21,834 P2, U.S. Plant Pat. No. 21,964 P2, and U.S. Plant Pat. No. 22,077 P2). *Opuntia ficus-indica* is a species of cactus that produces edible fruit and cladodes. The fruits can have large distinct surface spines, small hairy barbed glochids, or be mostly spineless. They are grown in arid parts of the world, such as Central America, South America, Spain, Italy, Israel and South Africa (Parish and Felker, 1997).

*Opuntia ficus-indica* fruit and the succulent vegetative pads or cladodes (modified stems) have chemotherapeutic medicinal properties that when consumed, can reportedly help improve human immune and nervous systems, reduce oxidative stress through scavenging free radicals, treat gastritis, reduce hyperglycemia, reduce atherosclerosis, inhibit diabetes and prostatic hypertrophy (enlarged prostate) (reviewed by Feugang et al., 2006). Uniquely, *Opuntia ficus-indica* fruit extracts are also reported to inhibit the growth of human ovarian, cervical and bladder cancer cell lines, and reduce the high rate of tumor formation in carcinogen-stressed nude mice (Zou et al., 2005).

The medicinal chemotherapeutic effects are at least in part a result of the antioxidant phytochemicals or pigments concentrated in *Opuntia ficus-indica* fruit and these compounds may help provide protection against multiple chronic human diseases. Polyphenolic flavonoids (quercetin, kaempferol and isorhamnetin), various carotenoids and the betalains (betanin and indicaxanthin) in the fruit are previously reported to have a high rate of antioxidant activity. Additionally, the fruit are rich in ascorbic acid and contain high levels of amino acids, especially proline, taurine and serine (Feugang et al., 2006). Cladodes from the *Opuntia ficus-indica* plant are naturally-enriched in niacin (B3), amino acids and fiber, and are reported to prevent excess blood sugar conversion into fat and lower total cholesterol, triglyceride and low density lipid levels.

Moreover, they contain elevated concentrations of vitamins A, B, and C. Also, *Opuntia ficus-indica* contains the following minerals: calcium, magnesium, sodium, potassium, and iron (Feugang et al., 2006). And *Opuntia ficus-indica* contains the following fibers: lignin, cellulose, hemicelluloses, pectin, mucilage's and gum form (Feugang et al., 2006). In addition, *Opuntia ficus-indica* contains 17 amino acids (Feugang et al., 2006). Organo-seleno forms are generally considered more bioavailable to antioxidant enzymes, i.e., selenoglutathione peroxidase (Stadtman, 1980), are easier to metabolize by humans, and are reported to have greater anticarcinogenic activity (Ip & Ganther, 1992; Clark et al., 1996).

BRIEF SUMMARY OF THE INVENTION

The present invention relates to a salt and boron tolerant cultivar of *Opuntia ficus-indica* named 'Seleno-Red.' The 'Seleno-Red' cultivar was identified from a cladode selection process to produce a *Opuntia ficus-indica* cultivar that is salt and boron tolerant, and can survive and readily accumulate selenium from the soils of the Western San Joaquin Valley region of California. The 'Seleno-Red' cultivar produces red flowers, cladodes without glochids, and fruit and cladodes containing high levels of selenium. Also, the 'Seleno-Red' cultivar exhibits a selenium volatilization rate of between approximately 58 $\mu g/m^2$/day and approximately 62 $\mu g/m^2$/day, when grown in soils containing a range of total selenium concentration from approximately 1.8 μg/g to approximately 5.3 μg/g. These traits have been repeatedly observed in asexually reproduced plants and are determined to be basic characteristics of the new salt and boron tolerant 'Seleno-Red' cultivar.

DETAILED BOTANICAL DESCRIPTION

Figure 1:
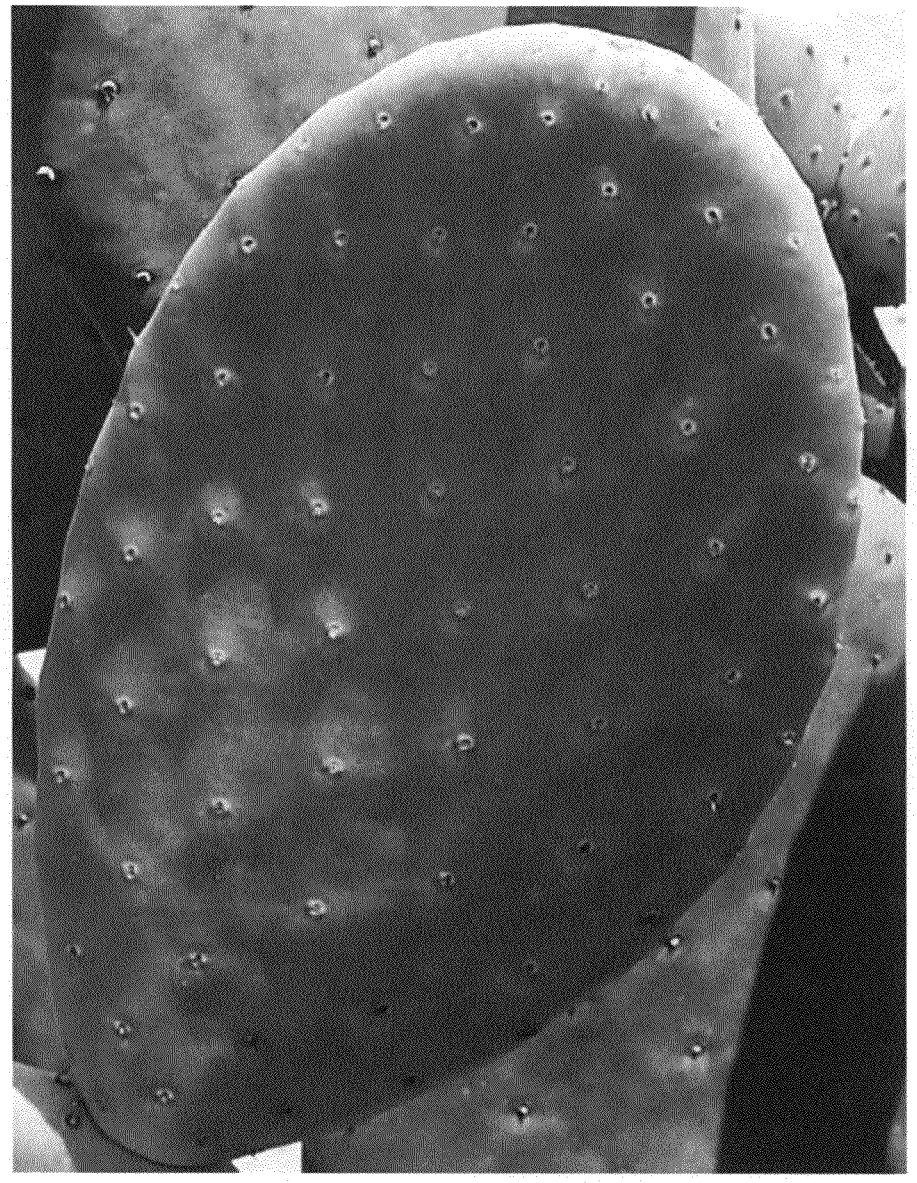
FIG. 1 shows the cladodes produced by the 'Seleno-Red' cultivar.

'Seleno-Red' is a cultivar of *Opuntia ficus-indica* identified through a cladode screening and cultigen selection program. 'Seleno-Red' is best described as a sport or a mutant with a uniquely expressed genotype, resulting in a phenotype allowing this unique individual to tolerate high concentration salt and boron conditions. 'Seleno-Red' is a cultivar that was asexually propagated from a spineless cactus pear (*Opuntia ficus-indica* (L. Mill) cultigen, which was selected from a cladode (stem) for its salt and boron tolerance from individual specimens growing at the USDA-ARS National Arid Land Genetic Resources Unit in Parlier, Calif. and at Red Rock Ranch in Five Points, Calif.

1. Cultivar Selection

The 'Seleno-Red' cultivar originated from a selection process to find salt and boron tolerant spineless individual cladodes or cultigens from approximately 300 *Opuntia ficus-indica* cactus pear plants among approximately 100 different accessions (naturally-occurring out crossing populations) that were collected from around the world, including accessions from Mexico, Chile, Brazil, Spain and Italy. The approximately 900 spineless cactus pear cladodes were individually screened in the greenhouse for their unique physiological ability to tolerate salt and boron, while producing quality fruit under these normally agronomically "toxic" poor soil conditions. To do this, approximately 900 cactus pear cladodes were initially planted in agricultural drainage sediment (transported to USDA-ARS Research Facility from the San Louis Drain) high in salt and high boron in order to stringently select for a cultigen with salt and boron tolerance at the San Joaquin Valley Research Center under greenhouse and microplot growing conditions.

Cuttings from randomly selected cladodes were made from the few selected survivors ~3 and then used for continued selection and propagation in the agricultural drainage sediment field microplots. These best three cultigens were allowed to grow into plants, which were monitored for any exhibition of salt or boron toxicity symptoms, such as necrosis of the leaf cladodes, dark, discolored cladode edges, abscised cladodes/fruit or often whole plant death. Individuals exhibiting the characteristic symptoms of salt and boron toxicity were noted and not chosen for future use.

Chemical properties of the agricultural drainage sediment within the microplots comprise of a salinity level ranging from approximately 4 decisiemens/m to approximately 6 decisiemens/m, soluble boron ranging from approximately 5 μg/ml to approximately 6 μg/ml, total selenium ranging from approximately 1.5 μg/g to approximately 5.5 μg/g, and extractable selenium ranging from approximately 0.5 μg/ml to approximately 1.5 μg/ml in 0-50 cm soil. Control soil (without salinity and selenium) comprised of a Hanford sandy loam, coarse-loamy (mixed superactive, nonacid, thermic Typic Xerothents), with a salinity of <1 decisiemen/m, total selenium of <0.1 μg/g, extractable selenium of <1 μg/ml, and soluble boron of <0.1 μg/ml was used to compare "normal-grown" vs. agriculture drainage-grown *Opuntia* plants.

After 36-48 months, cuttings were then made of best two tolerant plants (cultigens) surviving in salt and boron- drainage sediment microplots. After three months of initial root establishment, at least two salt and boron tolerant individual plant cultigens were identified and grown to an older maturity in the microplots at San Joaquin Valley Research Center, and harvested into individual cladodes or "cuttings". These two tolerant cultivars were propagated by placing cuttings of cladodes—dried and dipped in copper sulfate fungicide—into pots containing potting soil mix without irrigation until new root and cladode sprouts appeared after several weeks. The potted specimens were then lightly watered weekly with ⅕ strength Hoagland's solution for two months in a greenhouse before being hardened outside for one month. Once rooted in pots and new offshoots emerged they were planted in mass (~50 new plants) into the drainage- impacted soils high in salt, boron, and selenium, located in the harsh growing environment located at Red Rock Ranch under arid drought, and high temperature conditions.

The environment at Red Rock Ranch is very dry, hot, and exposed to high light intensity. The average summer (June-August) temperature at Red Rock Ranch ranges from a high of approximately 35 degrees C. during the day to a low of approximately 16 degrees C. at night. The average winter temperature (January and February) at Red Rock Ranch ranges from a high of approximately 12 degrees C. during the day to a low of approximately 3 degrees C. at night. The relative humidity ranges from approximately 28% to approximately 70% in the summer (June-August), and approximately 70% to approximately 95% in the winter (January and February). Horizontal solar radiation averages approximately 8 $kWh/m^2/d$ in July with an annual total ranging from approximately 1.8 $MWh/m^2$ to approximately 2.0 $MWh/m^2$. There is virtually no rainfall for four months from May through September, and evapotranspiration (ETo) remains high with daily rates of approximately 7 mm (7 $L/m^2/d$).

Red Rock Ranch has clay soils, containing high concentrations of salt ($Na_2SO_4$, NaCl, $CaCl_2$, $Na_2SeO_4$, $CaSO_4$, $Na_2B_4O_5(OH)_4$, and $CaB_3O_4(OH)_3$) and boron. The Red Rock Ranch soil composition is classified as an Oxalis silty clay loam (fine montmorillonitic, thermic Pachic Haploxeral) with a well-developed salinity profile. Soil salinity varies from approximately 4 μg/ml to approximately 8 μg/ml, while soluble boron varies from approximately 4 μg/ml to approximately 7 μg/ml. The top 30 cm of soil contains between approximately 2 μg Se/g and approximately 4 μg Se/g of total selenium, and the extractable selenium concentrations range between approximately 0.8 μg Se/mL and approximately 1.2 μg Se/mL.

Out of these approximately 50 cladodes transplanted into soils at Red Rock Ranch, a unique cultigen, emerged as the best growing and highest fruit producing *Opuntia ficus-indica* plant that produces red-purple fruit. This individual cultigen, apparently a unique sport or offshoot, was then clonally asexually propagated or cultivated as the most salt and boron tolerant 'Seleno-Red' cultivar, ideally suited for growth and fruit production the poor quality soils at Red Rock Ranch in the WSJV.

After 24 months, the 'Seleno-Red' cultivar now thrives in the hypersalinized Red Rock Ranch harsh field environment. Under these conditions, the 'Seleno-Red' cultivar has large cladodes, grows very well and produces large, firm fruit. 'Seleno-Red' cultivar is made from a salt and boron tolerant sport cultigen of *Opuntia ficus-indica*.

2. 'Seleno-Red' Cultivar Specification

The distinctive 'Seleno-Red' characteristics described below are reproduced asexually, propagated by cladode cuttings and replanting as described above. Color references are made to The Royal Horticultural Society Colour Chart (R.H.S.) 2001. Most measurements are taken from the 48-month old 'Seleno-Red' cultivar plant, surviving in the harsh Red Rock Ranch field environment, unless stated otherwise.

At two years old, the 'Seleno-Red' cultivar measures approximately 165 cm in height from the top of the plant to the soil level, approximately 150 cm in length from the tip of one cladode to the tip of an opposing cladode along a straight length axis, and approximately 125 cm in width from the tip of one cladode to the tip of an opposing cladode along a straight width axis, that is perpendicular to the length axis.

As shown in FIG. 1, the 'Seleno-Red' cultivar plant has a typical cladode that is broad, flat, and oval shaped. The cladode is Green 137C in color and the cladode surface has a smooth non-sticky texture. The typical cladode measures approximately 25 cm to approximately 26 cm in length, approximately 20 cm to approximately 21 cm in width, and approximately 2.8 cm to approximately 3.1 cm in thickness. The typical cladode may have between 160 and 170 areoles per cladode. The areoles on the cladodes are grey-orange group N167 A colored.

The cladode on 12-month old to 24-month old 'Seleno-Red' cultivar plant may have very small glochids on the cladodes. On the 12-month old to 24-month old 'Seleno-Red' cultivar plant, there may be 10 to 50 glochids per cladode, and each glochid may range from approximately 0:1 mm to approximately 1 mm in length. Older 'Seleno-Red' cultivar plants—which are those older than 24-months—have primarily only cladodes without any glochids. Therefore, the 'Seleno-Red' cultivar may be labeled as a "spineless cultivar."

Figure 2:
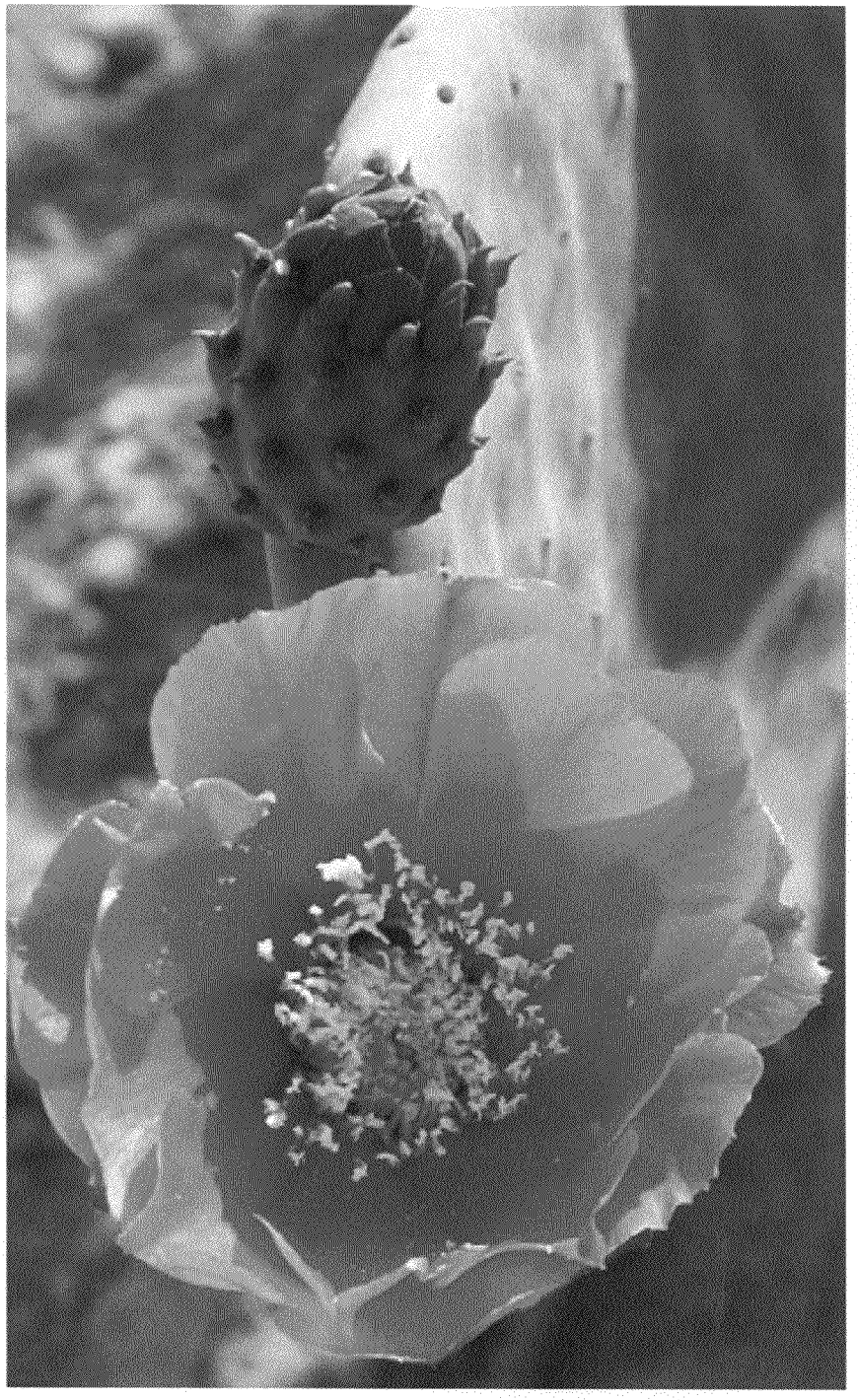
FIG. 2 shows an opened flower produced by and growing on the 'Seleno-Red' cultivar.

As shown in FIG. 2, the 'Seleno-Red' cultivar has petaled flowers measuring approximately 5 cm in diameter, with approximately 18 petals that are Orange 28A colored on the petal interior and 30A colored on the petal exterior. The flowers have no fragrance. The flower petals are oval shaped. The 'Seleno-Red' plant cultivar flowers from late July through mid-September and may be pollinated by honey bees and cactus bees. There is one stigma per flower, and the stigma length ranges from approximately 3 mm to approximately 7 mm (with an average length of 5 mm). There are approximately between 300 stamens and 700 stamens per flower (with an average of between 400 stamens and 500 stamens per flower), which range in length from approximately 300 mm to approximately 500 mm (with an average stamen length of about 400 mm).

Figure 3:
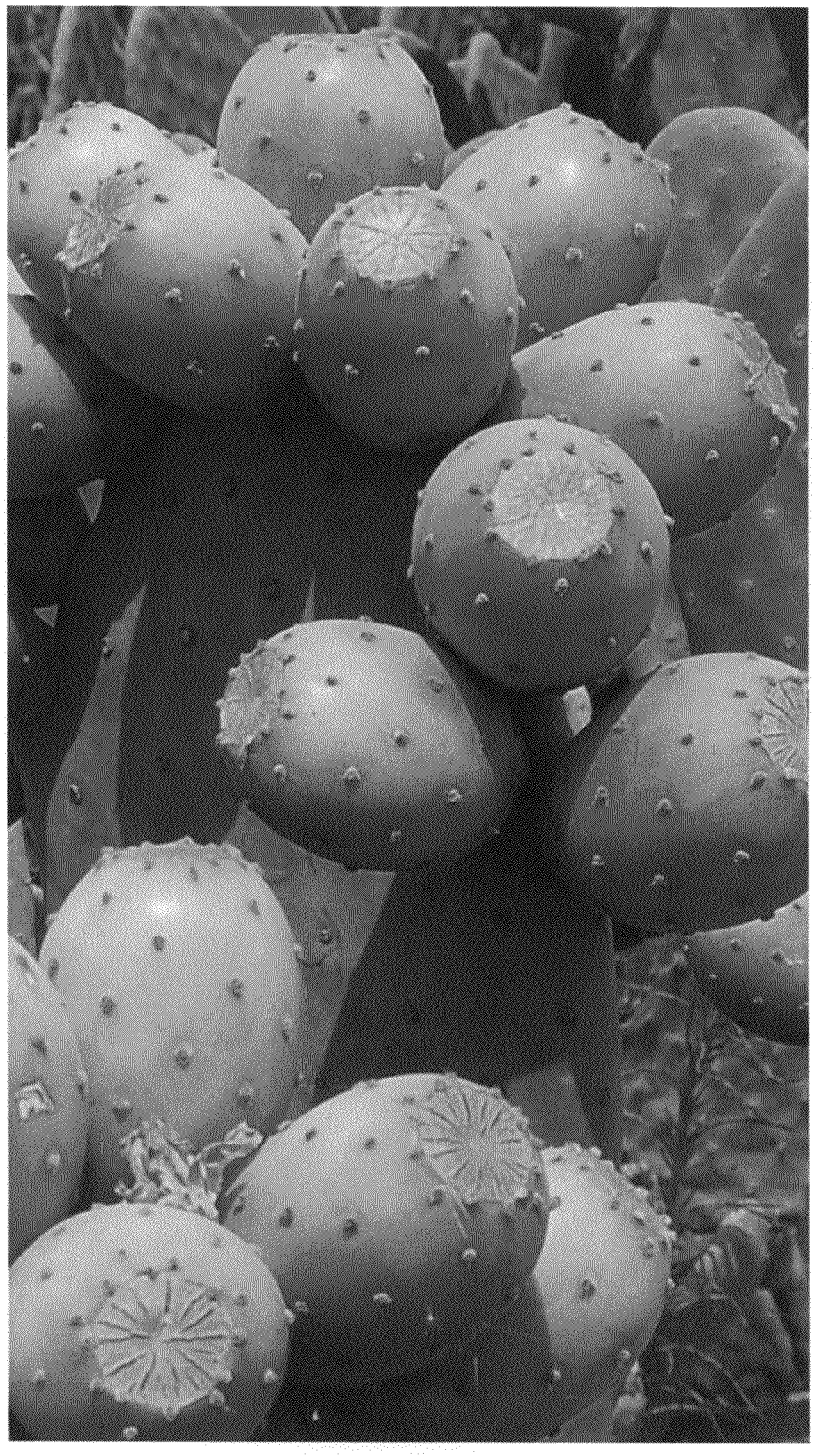
FIG. 3 shows fruit produced by and growing on the 'Seleno-Red' cultivar.

As shown in FIG. 3, the 'Seleno-Red' cultivar produces generally ovate-shaped fruit that are Red Purple 58A colored on the exterior and 59B to 65C colored in the interior. The fruit weighs approximately 100 g to approximately 120 g (with an average weight of approximately 109 g). There are approximately 35 to 50 areoles per fruit (with an average of approximately 44 areoles per fruit). There are very few, if any glochids on the areoles. The average number of glochids per areole ranges from 0 to approximately 3 (with an average number of glochids of 0 or 1). The length of the glochids range from approximately 0.1 mm to approximately 1 mm. The fruit has peel thickness ranging from approximately 3 mm to approximately 7 mm (with the average peel thickness being 5 mm).

The dry seed weight of the fruit ranges from approximately 1.5 g to approximately 2 g (with an average weight of approximately 1.77 g). The fruit is harvested based on the color intensity and desired firmness.

The 'Seleno-Red' cultivar contains a large amount of selenium in both the cladodes and the fruit when grown in soil that has between approximately 2 μg Se/g and 4 μg Se/g as total selenium in the upper 30 cm. The 'Seleno-Red' cultivar produced cladodes containing selenium ranging from approximately 8 μg Se/g and approximately 10 μg Se/g. The fruit peel contains between approximately 1.1 μg Se/g and 1.8 μg Se/g. The fruit flesh contains between approximately 1.5 μg Se/g and approximately 1.8 μg Se/g. The fruit seeds contain between approximately 3.5 μg Se/g and 3.8 μg Se/g. Plant tissue concentrations of selenium will vary dependent upon fluctuating amounts of soluble selenium and sulfate (competes for selenium uptake) salts present in the soil. Soil selenium concentrations and forms of selenium naturally fluctuate over time, as they are influenced by the soil environment.

In addition, the 'Seleno-Red' cultivar volatilizes selenium, a process otherwise described as the plant releasing selenium in gaseous form from the plant and adjacent soil surface. This process slowly removes selenium from the soil in a non-toxic manner. During the peak of summer (throughout the month of August) 'Seleno-Red' volatilizes between approximately 58 μg $Se/m^2$/day and approximately 62 μg $Se/m^2$/day when grown under the already described soil condition.

The 'Seleno-Red' cultivar differs in plant dimensions from other known *Opuntia ficus-indica* varieties. Table 1 shows the differences between the 'Seleno-Red' cultivar and the DAR 1-12-19 RED cultivar (U.S. Plant Pat. No. 21,760 P2). The 'Seleno-Red' cultivar was grown in soil with high levels of salt and boron. The DAR 1-12-19 RED cultivar was grown in conditions described in U.S. Plant Pat. No. 21,760 P2.

TABLE 1

'Seleno-Red' Compared to DAR 1-12-19 RED

| | 'Seleno-Red' | DAR 1-12-19 RED |
|---|---|---|
| Average Plant Height (cm) | 165 | 250 |
| Average Plant Width (cm) | 124 | 400 |
| Average Flower Diameter (cm) | 5 | 5 |
| Average Fruit Weight (g) | 109 | 125.4 |
| Average Cladode Length (cm) | 25.5 | 55 |
| Average Cladode Width (cm) | 20.3 | 20 |
| Average Cladode Thickness (cm) | 2.9 | 1.9 |

Besides differences in plant dimensions, due to its ability to survive and thrive in high saline and boron soils, the 'Seleno-Red' cultivar is able to accumulate substantial levels of selenium as shown in Table 2.

TABLE 2

Comparison of selenium content in 48-month old 'Seleno-Red' cultivar when grown in soil containing between 2 μg Se/g and 4 μg Se/g in comparison to control soils.

| | 'Seleno-Red' (with selenium) | 'Seleno-Red' (without selenium) |
|---|---|---|
| Selenium Content in Cladodes (μg Se/g) | 8-10 | 0.1 |
| Selenium Content in Fruit Peel (μg Se/g) | 1.1-1.8 | <0.1 |
| Selenium Content in Fruit Flesh (μg Se/g) | 1.5-1.8 | <0.1 |
| Selenium Content in Fruit Seeds (μg Se/g) | 3.5-3.8 | 0.1-0.2 |
| Selenium Volatilization Rate During Summer (μg $Se/m^2$/day) | 58-62 | <5 |

Disease or pest resistance has not been properly observed in the 'Seleno-Red' cultivar. However, the other individual cultigens all suffered both salt and boron toxicity in addition to an apparent pathogen susceptibility.

What is claimed is:

1. A new and distinct salt and boron tolerant, selenium accumulating cultivar of *Opuntia ficus-indica* named 'Seleno-Red,' as substantially illustrated and described herein.

* * * * *